United States Patent [19]

Heye et al.

[11] Patent Number: 4,476,110

[45] Date of Patent: Oct. 9, 1984

[54] BIOLOGICAL TREATMENT OF PLANTS

[75] Inventors: Christian C. Heye, Saeckingen, Fed. Rep. of Germany; John H. Andrews, Verona, Wis.

[73] Assignee: Wisconsin Alumni Research Foundation, Madison, Wis.

[21] Appl. No.: 376,346

[22] Filed: May 10, 1982

[51] Int. Cl.³ .................... A01N 63/00; A01N 65/00
[52] U.S. Cl. ..................................... 424/93; 424/195
[58] Field of Search .................................. 424/195, 93

[56] References Cited

PUBLICATIONS

W. Juelich, Monograph of the Athelieae, (Corticiaceae, Basidiomycetes) Willdenowia Beiheft, 7, pp. 62–64, 1972.

Primary Examiner—Albert T. Meyers
Assistant Examiner—John W. Rollins, Jr.
Attorney, Agent, or Firm—Quarles & Brady

[57] ABSTRACT

A method for controlling plant pathogens which grow on plant leaves, softening the leaves or accelerating the decomposition of the leaves comprises inoculating the leaves with *Athelia bombacina*. The method is effective in controlling apple scab.

4 Claims, No Drawings

BIOLOGICAL TREATMENT OF PLANTS

FIELD OF THE INVENTION

The present invention generally relates to the biological treatment of plants. More particularly, it relates to a method of inoculating plant leaves with the basidiomycete *Athelia bombacina* Pers. to control plant pathogens, to promote the softening of the leaves and to accelerate the decomposition of leaf litter.

DESCRIPTION OF PRIOR ART

Although the concept of biological control of plant disease is well established, most of the examples in practice involve soilborne pathogenic microorganisms. For example, W. A. Ayers and P. B. Adams recently patented an invention involving use of the mycoparasite, *Sporidesmium sclerotiorum*, to reduce sclerotia of susceptible pathogenic soil fungi (U.S. Pat. No. 4,246,258). There have been few successful practical attempts to apply biological methods against pathogens of aerial plant parts. A conspicuous accomplishment is the inoculation of pine stumps with the basidiomycete *Peniophora gigantea* to control a pathogenic basidiomycete, *Fomes annosus* (*Heterobasidion annosum*). Recently, G. A. Strobel patented an invention which uses a strain of the bacterium *Pseudomonas syringae* to control Dutch elm disease (U.S. Pat. No. 4,277,462). Elm trees are injected with *P. syringae* in a single treatment procedure.

The apple scab fungus, *Venturia inaequalis* Cke. Wint., attacks leaves and fruit of apples in the genus Malus. Although some success has been obtained by spraying leaves or leaf litter in the autumn with organic amendments which enhance leaf decomposition [see, e.g., R. T. Burchill et al., *Nature* 205: 520-521 (1965); J. E. Crosse et al., *Ann. Appl. Biol.* 61: 203-216 (1968); R. T. Burchill, *Ann. Appl. Biol.* 62: 297-307 (1968)], scab is controlled almost entirely by fungicides. To our knowledge, there is no prior report of the biological control of apple scab in practice on a commercial scale by use of any microbial agent.

BRIEF SUMMARY OF THE INVENTION

It is an object of the present invention to provide an effective, economically feasible means to control plant disease.

Another object is to increase the quantity and quality of crop yields by a biological method of controlling plant disease which is non-polluting.

Still another object is to provide a method employing a biological means to soften deciduous leaves.

A further object is to disclose a method of enhancing the rate of leaf decomposition.

A still further more specific object is to provide a method of reducing substantially or eliminating the fungus *Venturia inaequalis* Cke. Wint. from apple leaf litter and thereby impede or break the disease cycle resulting in control of the apple scab disease.

The above objects are attained by a method which comprises inoculating plant leaves or leaf litter with the basidiomycete *Athelia bombacina* Pers. The *Athelia bombacina* is preferably grown in or on sterilized culture media, an inoculum prepared containing the fungal propagules, nutrients and/or amendments, and the inoculum applied to the leaves or leaf litter.

DETAILED DESCRIPTION OF THE INVENTION

A serious fungal disease of apples (Malus spp.), caused by *Venturia inaequalis* Cke. Wint., is world-wide in distribution and causes significant economic losses. In addition to causing apple scab Venturia can cause early leaf drop and damage to the trees. In cold temperature geographic regions, the pathogen overwinters as a saprophyte and to a significant extent only as mycelium and incipient pseudothecia (sexual reproductive structures) in fallen apple leaves. Pseudothecia, initiated during fall or winter, mature in the spring to produce ascospores (sexual spores) which comprise the primary or initial inoculum for infection. Ascospores, ejected forcibly from wet leaf litter following rains, are dispersed by wind to unfolding leaves and expanding flowers. Following penetration of the host, the fungus develops structures which produce successive cycles of another type of spore (conidia), so the infection cycle repeats itself until leaf-fall in autumn. At that point, the overwintering saprophytic stage is re-initiated and Venturia expands into the decomposing leaf, where it must compete with other members of the microbial community.

We have discovered a method for the biological control of plant foliar pathogens that survive on leaf litter, such as the fungus *Venturia inaequalis*, which method employs the basidiomycete *Athelia bombacina* Pers., which was isolated during the winter of 1978, from decomposing apple leaf litter in an orchard near Arlington, Wis. (J. H. Andrews and C. M. Kenerley, *Can. J. Microbiol.* 25: 1331-1344. 1979). The microorganism has been identified by Dr. H. H. Burdsall of the U.S. Forest Products Laboratory (Madison, WI.) and a sub-culture is on deposit at the American Type Culture Collection (Rockville, MD) under accession No. 20629.

*Athelia bombacina* Pers. is described by Walter Juelich in the Monograph of the Athelieae (Corticiaceae, Basidiomycetes) WILLDENOWIA, Beiheft 7 (1972) pp. 283, pages 62-64, as having the following characteristics:

Fruiting Bodies: whitish to light cream colored, finely pinholed under magnification, on a loose, thick subiculum of hyaline hyphae, easily separable, tapering toward the edge.

Hyphae: hyaline, thin walled, basally sometimes thick walled ($0.3-0.4\mu$), diameter uniformly $3-5\mu$, clamps at all cross walls, branching at right angles or obliquely, mostly from clamps. Rhizomorphs absent, anastomoses rare.

Basidia: in clumps at the end of hyphae, most often from clamps, cylindrical to clavate, basally always with clamps, $12.5-16 \times 4-6.5\mu$. Sterigamata always 4, relatively long, outward pointing and slightly curved, about $5-6 \times 1-1.3\mu$.

Spores: young more or less spherical, later ellipsoid, with distinct apiculus, adaxial surface sometimes flattened, often glued together in groups of 2-4, not amyloid, hyaline, smooth, thin walled, $4.5-5.5-6 \times 2.5-3-(3.5)\mu$.

Substrate: *Abies alba* (wood), *A. balsamea* (wood, bark); *Larix dahurica* (bark); *Picea abies* (wood): *Pinus silvestris* (wood). Leaves: Betula, Populus, Quercus. Ferns: *Dryopteris filix-mas, Pteridium aquilinum*.

Distribution: Sweden, Finland, Czechoslovakia, Austria, USSR, Canada, U.S.A.

A key to identifying the species is also given by Eriksson, J. and Ryvarden, L. (1974) in The Corticiaceae of North Europe II, Fungiflora, Oslo, pp. 261 on page 98.

Although *A. bombacina* appears to be a natural inhabitant of apple leaf litter, our invention involves promoting its dominance in the microbial community. This is accomplished by growing the fungus on a suitable culture media, such as potato dextrose agar (PDA) or in sterile milled bran, and applying an inoculum containing the *A. bombacina* either as an aqueous suspension of fungal propagules with carboxymethylcellulose and a nutrient, such as yeast- and malt-extracts, or as colonized bran fragments to the plant leaves. The inoculum may be applied in the autumn to senescent but still attached leaves, or to detached leaves at the time when trees are naturally defoliating. In the case of apple leaves the *A. bombacina* readily colonizes the leaves or litter where it survives and, by its activities, inhibits the saprophytic, overwintering stage of Venturia, including formation of pseudothecia and ascospores.

Our method should also be effective against other plant pathogens including the fungi in the Venturia genus which cause damage to ornamentals and *Venturia pyrina* which causes scab or black spot on pears. Another benefit in our method is that leaves treated with *Athelia bombacina* become conspicuously softer and more pliable and decompose much more rapidly than non-treated control leaves. Thus, our method may be used to soften deciduous leaves for any purpose or to promote or accelerate the decomposition of deciduous leaves for various purposes including composting.

The *A. bombacina* can be applied to plants in aqueous medium with the application being most readily accomplished by suspending the propagules in such medium and spraying the suspension on the plants. If desired, a nutrient, which will aid in proliferation of the fungus on the plant after spraying, can be added to the inoculum. The addition of a binder, such as carboxymethylcellulose to the inoculum helps adhere the propagules to the leaves. It will be obvious that the concentration of propagules in the suspension can vary. It is also obvious that the rate of application of the propagule suspension will also vary depending upon the purpose for which it is applied and the method by which it is applied, e.g. aerial or ground rig spraying. In all cases, sufficient of the Athelia propagules is to be applied to achieve the desired result and applying too much will not be economical and should be avoided.

The importance of the rate of deposition for the amount of Athelia deposited on the plant is not significant since the fungus propagates very rapidly, especially when deposited on the plants in nutrient media. In laboratory tests, the fungus has been applied by liquid spray in which the fungus is suspended in nutrient solution. It may be possible to dust dried fungus onto the plant as a powder, preferably with a powdered carrier as diluent and/or nutrient medium.

The exact mechanism by which the *Athelia bombacina* acts to control plant pathogen growth has not yet been established. It appears to be acting as a competitor which colonizes rapidly to crowd out, prevent or preclude the growth of the plant pathogen and/or it also could be functioning as an inhibitor or antibiotic which destroys the plant pathogens or prevents them from growing. Whatever the mechanism, the application of *Athelia bombacina* has been found to be effective to eliminate the ascospores and control the growth of

*Venturia inaequalis* and to soften and speed the decomposition of apple leaves.

EXAMPLES

Laboratory experiments were designed to answer the following questions: what effect does Athelia have on (i) formation of pseudothecia; on (ii) production of ascospores by the pathogen; and (iii) on leaf decomposition as measured by loss in leaf strength? Questions (i) and (iii) were addressed using sterilized leaf material, artificially-inoculated with *Venturia inaequalis* and subsequently inoculated with the antagonist. Question (ii), which is the more important one in terms of usefulness of any biocontrol agent for this system, was answered using unsterile leaves in vitro, naturally infected with *V. inaequalis* and inoculated with the antagonist.

I

Experiments with sterilized apple leaves to test the effect of Athelia on Venturia inaequalis and leaf decomposition.

Discs (2.54 $cm^2$) were cut from green and senescent leaves of *Malus pumila* Mill. var. McIntosh which were detached from the tree (green) or picked off the ground (senescent) in early and late October, respectively. Discs were sterilized in plastic 15 ml vials by gamma irradiation (36.6 Mrad) from a 2000 Ci, $^{137}Cs$ source. Discs were then placed aseptically in sterile 200 ml screw cap vials containing 10 ml vermiculite and 8 ml water.

Discs in these vials were inoculated with two compatible, i.e. pseudothecia-forming strains of *V. inaequalis* at $5\times10^4$ conidia/disc. The basic methodology for obtaining conidia is described by C. J. Nusbaum and G. W. Keitt. [*J. Agr. Res.* 56: 595–618 (1938)]. Discs for evaluating the effect of Athelia were also inoculated two weeks later with the antagonist as a 0.4 $cm^2$ plug cut from a 16-day-old potato dextrose agar (PDA) culture of the organism, or as basidiospores in 0.02M phosphate buffer (pH 8) at $5\times10^4$ spores/leaf disc. Each treatment consisted of 10 leaf discs.

All discs were incubated at ambient laboratory temperature for one week following inoculation of the antagonist and then at 4° C. for approximately 6 months during which time the pathogen formed pseudothecia.

The effect of Athelia on Venturia was judged by evaluating its ability to colonize the leaf disc and to inhibit the formation of setose (i.e. mainly mature) and of total (i.e. both setose and incipient) pseudothecia. Both categories of pseudothecia were therefore counted under a dissecting microscope after clearing the leaf disc in chlorine gas. The effect of Athelia on leaf decomposition was evaluated by determining leaf strength of control and Athelia-treated leaves. Leaf strength was measured as the force necessary to punch through a disc with a Chatillon (Model DPP-b 500 g) penetrometer to which a 6 mm diameter probe with a point in form of an inverted V was attached. Leaf discs were held between two sheets of plexiglass with a series of holes allowing passage of the probe through the disc. Force was recorded in dynes.

The results of the experiments are summarized in Table 1. Data are $\log_{10}$ or square root transformed, as indicated, to meet the requirements of the underlying statistical tests. Differences between senescent and green leaves are usually not substantial and the results for the two data sets can therefore be discussed concurrently. The major finding from this experiment was that Athelia can prevent the formation of setose pseudothecia and inhibit the formation of incipient pseudothecia. However, this requires that the antagonist colonize the disc extensively, as was observed when Athelia was inoculated with a plug of PDA. Athelia, when applied as basidiospores, colonized the disc, although to a much lesser extent; it prevented formation of setose pseudothecia but was less inhibitory to pseudothecial initials.

Athelia also reduced leaf strength significantly, i.e. leaf discs colonized by the antagonist were measurably softer than either sterile discs or those inoculated by Venturia alone.

In a second experiment conducted on green discs only, Athelia prevented formation of both setose and incipient pseudothecia entirely.

Basidiospores appear to be a less desirable form of inoculum in terms of colonization of discs, and agar plugs appear to be unfeasible in view of future practical applications. Therefore, other forms of inocula were evaluated as follows:

washed in sterile buffer until the supernatant after centrifugation was clear (usually two washes). The macerate was then mixed aseptically at about one gram wet weight of macerate per ml of buffer or CMY respectively. CMY was prepared by mixing carboxymethylcellulose (0.9% w/v), malt extract (1.125% w/v), and yeast extract (0.45% w/v) in water. The Athelia/buffer and the Athelia/CMY combination were both applied at a rate of 620 viable propagules/$cm^2$ to the respective discs.

For milled bran cultures, the wheat bran was milled and sieved to a particle size 300 μm and mixed at a rate of 1:3 w/v with water. This medium was autoclaved in 500 ml Erlenmeyer flasks and inoculated with Athelia. The bran particles were colonized after 30 days and were then washed and finally suspended in sterile buffer at a ratio of 1:10 original dry weight of bran to volume of buffer. This suspension of colonized bran particles was applied to the discs at a rate of 25 viable propagules/$cm^2$ of disc. Each treatment consisted of 50 leaf discs. Uninoculated, CMY inoculated and bran-

TABLE 1

Colonization of sterile apple leaf discs by *Athelia bombacina* and effects of this antagonist on formation of pseudothecia by *Venturia inaequalis* and on leaf strength

| Treatment | Leaf Age[c] | Athelia Colonization[d] Mean | SE | Pseudothecia[e] Setose Mean | SE | Total Mean[g] | SE | Leaf[f] Strength Mean[g] | SE |
|---|---|---|---|---|---|---|---|---|---|
| Sterile Control | G |  |  |  |  |  |  | 188 A | 13 |
|  | S |  |  |  |  |  |  | 175 | 12 |
| Venturia[a] + Agar Plug | G |  |  | 1.23 | 0.12 | 1.89 | 0.11 | 195 A | 11 |
|  | S |  |  | 0.97 | 0.12 | 1.94 | 0.08 | 198 A | 10 |
| Athelia P[b] | G | 4.9 | 0.1 | 0 | 0 | 0.23 | 0.16 | 100 B | 13 |
|  | S | 5.0 | 0 | 0 | 0 | 0 | 0 | 93 B | 17 |
| Athelia S[b] | G | 2.2 | 0.1 | 0 | 0 | 0.72 | 0.21 | 124 C | 5 |
|  | S | 2.0 | 0 | 0 | 0 | 0.09 | 0.42 | 135 | 9 |

[a]Conidia of two compatible strains at 5 × $10^4$ spores/disc.
[b]Inoculated as (P) plug (0.4 $cm^2$) of PDA culture or as (S) basidiospores in 0.02M phosphate buffer at 5 × $10^4$ spores/disc.
[c]Leaf discs (2.54 $cm^2$) cut from senescent (S) or green (G) leaves. Sterilized by gamma irradiation.
[d]Rated visually on a scale from 1 = not colonized to 5 = surface 100% colonized.
[e]$Log_{10}$ transformed counts + 1. Total = initial + setose P.
[f]As force in dynes (square root transformed) determined with a penetrometer and 6 mm diameter probe.
[g]In each column means followed by the same letter do not differ significantly according to Duncan's Multiple Range tests. α = 0.01, performed on combined data for green and senescent. Mean and standard error (SE) of usually 10 discs/treatment.

II

Experiments with non-sterile apple leaves to test the effect of Athelia on *V. inaequalis*.

Discs (2.54 $cm^2$) were cut from green leaves naturally-infected with *V. inaequalis* collected about Oct. 15, 1981 from *Malus pumila* Mill. var. McIntosh trees. The discs were placed aseptically into sterile screw cap vials as described in Experiment I.

Athelia, for treatments listed in Table 2, was grown for inoculum production on PDA or milled bran. For PDA cultures, the agar surface in the petri plate was covered with dialysis membrane. This technique is described by C. Gagnon in *Stain Technology* 41: 247 (1966) and is hereby incorporated by reference into this application. Athelia forms a thick hymenium-like layer with basidia and basidio-spores on this membrane and can easily be separated from agar and membrane.

The inoculum was produced as follows: The mycelial layers were peeled off 16-day old cultures, macerated in sterile buffer in a sterile Sorval Omni Mixer, and inoculated discs served as controls. The vials with the inoculated discs were incubated at 16° C. for 8 days and then at 4° C. for about 6 months.

To determine ascospore production, discs were attached with petroleum jelly to the inside of the covers of 5 cm diameter petri dishes (5 discs per lid). The discs were moistened with distilled water from an aspirator to trigger ascospore discharge into the bottom of the dish which contained water with 0.05% Tween 20 and 0.02% $NaN_3$. Discs were kept humid for 72 h. Ascospores sunk to the bottom of the dish and were counted with a compound microscope. Ascospore yield was expressed as $log_{10}$ spores + 1/$cm^2$ of leaf disc.

The assay detected ascospores from at least 70% of all pseudothecia. This relative insensitivity is however immaterial in view of the fact that there are generally no spore-bearing pseudothecia made either on sterilized discs as shown above or on naturally-infected discs inoculated with Athelia, as shown in another experiment.

As seen in Table 2, no ascospores were produced on discs that were extensively colonized by the antagonist following Athelia/buffer or Athelia/CMY inoculations. Discs inoculated with Athelia/bran were less well colonized than those of the other two Athelia treatments; however, ascospore productivity was still significantly lower than on control discs.

TABLE 2

Colonization in vitro by *Athelia bombacina* of non-sterile green apple leaf discs naturally infected by *Venturia inaequalis* and effect of the antagonist on ascospore production by the pathogen

| Treatments | Athelia colonization[e] | Ascospores[f] Mean[g] | SE |
|---|---|---|---|
| Uninoculated | 0 | 1.894 A | 0.131 |
| CMY[a] | 0 | 2.256 A | 0.170 |
| Bran[b] | 0 | 1.871 A | 0.277 |
| Athelia[c] | 98 | 0 | 0 |
| Athelia/CMY[c] | 100 | 0 | 0 |
| Athelia/Bran[d] | 20 | 1.191 B | 0.205 |

[a]CMY = Carboxymethylcellulose (0.9% w/v) + malt extract (1.125% w/v) + yeast extract (0.45% w/v) in water.
[b]Wheat bran milled to particles size ≦300 μm.
[c]Applied as macerated PDA cultures suspended in water or CMY at 620 viable propagules/cm² of disc.
[d]Grown on ≦300 μm particle size bran suspended in water and applied at 25 viable propagules/cm² of disc.
[e]As % of 50 discs visually colonized.
[f]Log 10 ascospores + 1/cm² of leaf, mean and standard error (SE) of usually 10, 5-disc samples.
[g]Means followed by same letter not significantly different according to Duncan's Multiple Range Test, α = 0.05.

III

Field Experiment

The purpose of this experiment was to evaluate the impact of Athelia on ascopore production and on decomposition of leaves under field conditions.

Apple leaves naturally infected by *V. inaequalis* were detached in autumn from a *Malus pumila* Mill. var. McIntosh tree which was 50% naturally-defoliated. The leaves were returned to the laboratory and six, 100-leaf replicates were randomly assigned to each treatment listed in Table 3. Their dry weight was determined by subsampling leaves and drying them to constant weight in an oven at 80° C.

The inoculum was grown as described in experiment II above. The inocula were applied individually to each of the six, 100-leaf replicates of a treatment by spraying both surfaces of the leaves with an aspirator type sprayer. The sprayer consisted of two stainless steel tubes of 3 mm inner diameter at right angles to each other; $70 \times 10^4$ dynes/cm² pressure was applied to one of the tubes resulting in deliverance of the antagonist suspension from the other as a spray at a rate of 110 ml/min. Athelia/CMY and Athelia/bran were thus applied respectively at rates of 620 and 25 viable propagules/cm² leaf surface. Leaves were then sealed in nylon mesh (15 μm holes) bags, incubated in a 16° C. incubator for one week, and then placed on the ground in a randomized complete block design in an orchard near Arlington, Wis.

At bud break stage of the apple trees the following spring, leaves were returned to the laboratory and kept at 4° C. when not being assayed for spores or weight. Dry weight of leaves was determined by subsampling leaves and drying them to constant dry weight in an oven at 80° C. to calculate a wet-dry weight conversion factor for all main samples. The average dry weight loss in percent from fall to spring is recorded in Table 3.

Colonization of leaves by the antagonist was determined by attempting to reisolate Athelia from the leaves. One disc of 0.2 cm² was cut from each of 270 leaves/treatment. Discs were surface-sterilized for 5 min in 10% commercial bleach, rinsed in 10% bleach and in water and plated 15/petri plate of PDA containing chloramphenicol (250 ppm) and novobiocin (100 ppm). Colonization was recorded as the average number of successful reisolations per plate and treatment.

To determine ascospore productivity, the leaves from each of the six, 100-leaf samples (=1 bag)/treatment were subdivided into 5-6 subsamples of 200 cm² total leaf area using an electronic leaf area meter. Ascospores were collected from both surfaces of these 200 cm² area leaf subsamples using a modified version of an aspiration technique described by J. D. Gilpatrick et al. in *Plant Disease Reporter* 56: 39-42 (1972). Collected spores were counted with a hemacytometer. These counts were $\log_{10}$ transformed. Averages per treatment are shown in Table 3.

Leaf strength, an indicator for leaf decomposition in addition to dry weight loss, was determined as described above, using discs (2.14 cm² each) cut from 6×20 leaves/treatment.

Results are summarized in Table 3. Leaves treated with Athelia/CMY were better colonized than those treated with Athelia/bran. No ascospores of Venturia were produced on the Athelia-inoculated leaves compared to large amounts on the controls. Leaf decomposition, as measured by loss of dry weight and of leaf strength, was increased on Athelia/CMY treated leaves compared to the other treatments. These leaves lost about 13% more dry weight from fall to spring and were also much softer than controls. These differences were statistically significant.

TABLE 3

*Athelia bombacina* colonization of apple leaves under field conditions and its impact on leaf strength, dry weight loss, and ascospore production by *Venturia inaequalis*

| Treatment | Athelia colonization[e] Mean[i] | SE | Leaf strength[f] Mean[i] | SE | % Loss g dry weight Mean[i] | SE | Ascospores[h] Mean[i] | SE |
|---|---|---|---|---|---|---|---|---|
| Buffer | 0 | 0 | 133 A | 4 | 17.7 A | 2.5 | 3.9 | 0.2 |
| CMY[a] | 0 | 0 | 101 B | 3 | 20.0 A | 1.6 | 3.1 | 0.2 |
| Bran[b] | 0 | 0 | 112 B | 4 | 18.4 A | 1.4 | 3.5 | 0.2 |
| Athelia/CMY[c] | 9.9 A | 0.5 | 78 C | 9 | 33.7 B | 2.0 | 0 | 0 |

TABLE 3-continued

*Athelia bombacina* colonization of apple leaves under field conditions and its impact on leaf strength, dry weight loss, and ascospore production by *Venturia inaequalis*

| Treatment | Athelia colonization[e] | | Leaf strength[f] | | % Loss g dry weight | | Ascospores[h] | |
|---|---|---|---|---|---|---|---|---|
| | Mean[i] | SE | Mean[i] | SE | Mean[i] | SE | Mean[i] | SE |
| Athelia/Bran[d] | 3.4 | B 0.4 | 58 C | 8 | 23.6 A | 1.7 | 0 | 0 |

[a]CMY = carboxymethylcellulose (0.9% w/v) + malt extract (1.125% w/v) + yeast extract (0.45% w/v) in 0.02M phosphate buffer (pH 8).
[b]Wheat bran milled to particle size $\leq 300$ μm, in buffer.
[c]Sprayed as macerate of PDA culture suspended in CMY at 620 viable propagules/cm$^2$ of leaves.
[d]Grown on $\leq 300$ μm wheat bran suspended in buffer for application at 25 viable propagules/cm$^2$ of leaves.
[e]Average successful reisolations/plate, 15 attempted reisolations/plate, 270 attempts/treatment.
[f]In 1000 dynes determined with penetrometer with a 6 mm diameter probe on 6 × 20 leaves/treatment.
[g]From fall to spring, means of 6 replications/treatment.
[h]$\text{Log}_{10}$ ascospores + 1/400 cm$^2$ of leaves. Means of 6 × 6 measurements/treatment. SE = standard error.
[i]In each column means followed by the same letter do not differ significantly according to Duncan's Multiple Range tests $\alpha = 0.05$ for leaf strength, $\alpha = 0.01$ for weight loss and colonization.

It will be readily apparent to those skilled in the art that the foregoing description has been for purpose of illustration and that a number of modifications and changes may be made without departing from the spirit and scope of the present invention. For example, although a specific strain of *A. bombacina* was employed, any artificially induced or naturally arising strain or biotype that provides satisfactory results can be used. It also will be apparent that other inoculum formulations, culture media and methods of application, other than those described, may be used. Therefore, it is intended that the invention not be limited except by the claims which follow:

We claim:

1. The method of controlling the damage caused by *Venturia inaequalis* to apple trees which comprises adding to apple tree leaves or leaf litter an effective amount of *Athelia bombacina* to insure the dominance of the *Athelia bombacina* in the microbial community on the apple tree leaves inaequalis.

2. The method of claim 1 in which the *Athelia bombacina* is added in the form of an inoculum comprising fungal propagules suspended in an aqueous medium.

3. The method of claim 1 in which the *Athelia bombacina* is added in the form of colonized bran fragments.

4. An inoculant for adding *Althelia bombacina* to the leaves or leaf litter of apple trees which comprises fungal propagules of *Athelia bombacina* in combination with an effective amount of carboxymethylcellulose binder for fixing the *Athelia bombacina* to the leaves or leaf litter.

* * * * *

UNITED STATES PATENT AND TRADEMARK OFFICE
CERTIFICATE OF CORRECTION

PATENT NO. : 4,476,110
DATED : October 9, 1984
INVENTOR(S) : Heye et al

It is certified that error appears in the above-identified patent and that said Letters Patent is hereby corrected as shown below:

Column 4, line 56, "DPP-b 500" should read ---DPP-500---

Column 10, line 23, After "leaves" insert ---or leaf litter thereby inhibiting the growth of Venturia---

Signed and Sealed this

Fourth Day of June 1985

[SEAL]

Attest:

DONALD J. QUIGG

Attesting Officer   Acting Commissioner of Patents and Trademarks